US009795696B2

(12) United States Patent
Markel

(10) Patent No.: US 9,795,696 B2
(45) Date of Patent: Oct. 24, 2017

(54) CEACAM1 BASED CANCER THERAPY AND DIAGNOSIS

(75) Inventor: Gal Markel, Haifa (IL)

(73) Assignee: Gal Markel, Haifa (IL)

(*) Notice: Subject to any disclaimer, the term of this patent is extended or adjusted under 35 U.S.C. 154(b) by 0 days.

(21) Appl. No.: 11/423,386

(22) Filed: Jun. 9, 2006

(65) Prior Publication Data

US 2007/0071758 A1 Mar. 29, 2007

Related U.S. Application Data

(60) Provisional application No. 60/689,316, filed on Jun. 9, 2005.

(51) Int. Cl.
G01N 33/574 (2006.01)
A61K 51/10 (2006.01)
A61K 49/00 (2006.01)
C07K 16/30 (2006.01)
G01N 33/569 (2006.01)
A61K 38/17 (2006.01)
A61K 35/17 (2015.01)
C07K 14/705 (2006.01)
C12N 5/0781 (2010.01)
C12N 5/0783 (2010.01)
A61K 51/04 (2006.01)
A61K 51/08 (2006.01)
A61K 35/12 (2015.01)

(52) U.S. Cl.
CPC .............. A61K 51/10 (2013.01); A61K 35/17 (2013.01); A61K 38/1774 (2013.01); A61K 49/0004 (2013.01); A61K 49/0052 (2013.01); A61K 49/0056 (2013.01); A61K 49/0058 (2013.01); A61K 51/04 (2013.01); A61K 51/088 (2013.01); C07K 14/70503 (2013.01); C07K 16/3007 (2013.01); C12N 5/0635 (2013.01); C12N 5/0636 (2013.01); G01N 33/56972 (2013.01); G01N 33/574 (2013.01); G01N 33/57492 (2013.01); A61K 2035/122 (2013.01); C07K 2317/54 (2013.01); C07K 2317/732 (2013.01); G01N 2333/70596 (2013.01)

(58) Field of Classification Search
CPC ............ A61K 49/0058; A61K 2123/00; C07K 16/3007; C07K 16/2896; C07K 16/00–16/468; C07K 2319/40–2319/43; C07K 2319/60; C07K 2319/61; C07K 2317/62–2317/626; G01N 33/56972; G01N 33/57473; G01N 33/574; G01N 33/5743; G01N 33/5748; G01N 2333/705
See application file for complete search history.

(56) References Cited

U.S. PATENT DOCUMENTS

| | | | | |
|---|---|---|---|---|
| 5,977,322 A | * | 11/1999 | Marks et al. | 530/388.85 |
| 6,852,320 B2 | | 2/2005 | Blumberg | |
| 8,598,322 B2 | * | 12/2013 | Markel et al. | 530/388.8 |
| 2002/0028203 A1 | * | 3/2002 | Blumberg | 424/145.1 |
| 2003/0022292 A1 | * | 1/2003 | Gray-Owen | C07K 14/22 435/69.1 |
| 2004/0047858 A1 | | 3/2004 | Blumberg et al. | |
| 2012/0100158 A1 | * | 4/2012 | Markel et al. | 424/174.1 |
| 2014/0120554 A1 | * | 5/2014 | Markel et al. | 435/7.23 |
| 2014/0271618 A1 | * | 9/2014 | Markel et al. | 424/131.1 |

OTHER PUBLICATIONS

Satoh et al, 2002, J Clin Lab Analysis, 16: 79-85.*
Eckart Laack et al, 2002, J Clin Oncol, 20(21): 4279-4283.*
Allum et al, 1987, NCI monogr 3: 11-17.*
Reilly et al, 1997, Clin Pharmacokinet. 32(4): 313-323.*
Gray-Owen & Blumberg, Nat. Rev. Immunol. 2006; 6:433-46.*
Thies et al., J Clin Oncol 2002; 20:2530-36.*
Kammerer et al. J. Pathol 2004; 204:258-67.*
Roussel et al., Cancer Immunol Immunother 1995; 41:1-9.*

* cited by examiner

Primary Examiner — Jessica H Roark
(74) Attorney, Agent, or Firm — McAndrews, Held and Malloy

(57) ABSTRACT

The present invention provides methods for detecting CEACAM1 expression in a cancer patient. In particular, methods according to the present invention include contacting a biological sample having Tumor Infiltrating Lymphocytes expressing CEACAM1 with an anti-CEACAM1 antibody labeled with a detectable moiety.

2 Claims, No Drawings

SEQUENCE LISTING

```
<160> NUMBER OF SEQ ID NOS: 4

<210> SEQ ID NO 1
<211> LENGTH: 108
<212> TYPE: PRT
<213> ORGANISM: Homo Sapiens
<220> FEATURE:
<221> NAME/KEY: MISC_FEATURE
<223> OTHER INFORMATION: CEACAM1 N-terminal domain

<400> SEQUENCE: 1

Gln Leu Thr Thr Glu Ser Met Pro Phe Asn Val Ala Glu Gly Lys Glu
1               5                   10                  15

Val Leu Leu Leu Val His Asn Leu Pro Gln Gln Leu Phe Gly Tyr Ser
            20                  25                  30

Trp Tyr Lys Gly Glu Arg Val Asp Gly Asn Arg Gln Ile Val Gly Tyr
        35                  40                  45

Ala Ile Gly Thr Gln Gln Ala Thr Pro Gly Pro Ala Asn Ser Gly Arg
    50                  55                  60

Glu Thr Ile Tyr Pro Asn Ala Ser Leu Leu Ile Gln Asn Val Thr Gln
65                  70                  75                  80

Asn Asp Thr Gly Phe Tyr Thr Leu Gln Val Ile Lys Ser Asp Leu Val
                85                  90                  95

Asn Glu Glu Ala Thr Gly Gln Phe His Val Tyr Pro
            100                 105

<210> SEQ ID NO 2
<211> LENGTH: 108
<212> TYPE: PRT
<213> ORGANISM: Homo Sapiens
<220> FEATURE:
<221> NAME/KEY: MISC_FEATURE
<223> OTHER INFORMATION: CEACAM3  N-terminal domain

<400> SEQUENCE: 2

Lys Leu Thr Ile Glu Ser Met Pro Leu Ser Val Ala Glu Gly Lys Glu
1               5                   10                  15

Val Leu Leu Leu Val His Asn Leu Pro Gln His Leu Phe Gly Tyr Ser
            20                  25                  30

Trp Tyr Lys Gly Glu Arg Val Asp Gly Asn Ser Leu Ile Val Gly Tyr
        35                  40                  45

Val Ile Gly Thr Gln Gln Ala Thr Pro Gly Ala Ala Tyr Ser Gly Arg
```

-continued

```
            50                  55                  60

Glu Thr Ile Tyr Thr Asn Ala Ser Leu Leu Ile Gln Asn Val Thr Gln
 65                  70                  75                  80

Asn Asp Ile Gly Phe Tyr Thr Leu Gln Val Ile Lys Ser Asp Leu Val
                 85                  90                  95

Asn Glu Glu Ala Thr Gly Gln Phe His Val Tyr Gln
            100                 105

<210> SEQ ID NO 3
<211> LENGTH: 108
<212> TYPE: PRT
<213> ORGANISM: Homo Sapiens
<220> FEATURE:
<221> NAME/KEY: MISC_FEATURE
<223> OTHER INFORMATION: CEACAM5 N-terminal domain

<400> SEQUENCE: 3

Lys Leu Thr Ile Glu Ser Thr Pro Phe Asn Val Ala Glu Gly Lys Glu
  1               5                  10                  15

Val Leu Leu Leu Val His Asn Leu Pro Gln His Leu Phe Gly Tyr Ser
                 20                  25                  30

Trp Tyr Lys Gly Glu Arg Val Asp Gly Asn Arg Gln Ile Ile Gly Tyr
             35                  40                  45

Val Ile Gly Thr Gln Gln Ala Thr Pro Gly Pro Ala Tyr Ser Gly Arg
         50                  55                  60

Glu Ile Ile Tyr Pro Asn Ala Ser Leu Leu Ile Gln Asn Ile Ile Gln
 65                  70                  75                  80

Asn Asp Thr Gly Phe Tyr Thr Leu His Val Ile Lys Ser Asp Leu Val
                 85                  90                  95

Asn Glu Glu Ala Thr Gly Gln Phe Arg Val Tyr Pro
            100                 105

<210> SEQ ID NO 4
<211> LENGTH: 108
<212> TYPE: PRT
<213> ORGANISM: Homo Sapiens
<220> FEATURE:
<221> NAME/KEY: MISC_FEATURE
<223> OTHER INFORMATION: CEACAM6 N-terminal domain

<400> SEQUENCE: 4

Lys Leu Thr Ile Glu Ser Thr Pro Phe Asn Val Ala Glu Gly Lys Glu
  1               5                  10                  15

Val Leu Leu Leu Ala His Asn Leu Pro Gln Asn Arg Ile Gly Tyr Ser
                 20                  25                  30

Trp Tyr Lys Gly Glu Arg Val Asp Gly Asn Ser Leu Ile Val Gly Tyr
             35                  40                  45

Val Ile Gly Thr Gln Gln Ala Thr Pro Gly Pro Ala Tyr Ser Gly Arg
         50                  55                  60

Glu Thr Ile Tyr Pro Asn Ala Ser Leu Leu Ile Gln Asn Val Thr Gln
 65                  70                  75                  80

Asn Asp Thr Gly Phe Tyr Thr Leu Gln Val Ile Lys Ser Asp Leu Val
                 85                  90                  95

Asn Glu Glu Ala Thr Gly Gln Phe His Val Tyr Pro
            100                 105
```

CEACAM1 BASED CANCER THERAPY AND DIAGNOSIS

CROSS-REFERENCE TO RELATED APPLICATIONS/INCORPORATION BY REFERENCE

The present application is related to and claims priority from U.S. Provisional Patent Application Ser. No. 60/689,316, filed Jun. 9, 2005, and titled "THE MODULATION OF IMMUNITY AND CEACAM1 ACTIVITY," the contents of which are hereby incorporated herein by reference in their entirety. Additionally, all cited references in the present application are incorporated by reference in their entirety.

FIELD OF THE INVENTION

The invention relates to methods and compositions for the treatment and diagnosis of cancers expressing CEACAM1. At least one object of the present invention relates to methods and compositions for enhancing the efficacy of tumor-infiltrating lymphocyte (TIL) therapy in the treatment of cancer.

BACKGROUND OF THE INVENTION

Immune system cells found deep inside tumor tissue have been named tumor-infiltrating lymphocytes (TILs). These cells can be removed from tumor samples taken from a patient and forced to reproduce by treating them with IL-2. When injected back into the patient, these cells often become active cancer fighters. (Rosenberg S A, Speiss P, Lafreniere R. *A new approach to the adoptive immuno-therapy of cancer with tumor-infiltrating lymphocytes.* Science. 1986; 233:1318-1321.) (Rosenberg S A., et al., Use of tumor-infiltrating lymphocytes and interleukin-2 in the immunotherapy of patients with metastatic melanoma. A preliminary report. N Engl J Med. 1988 Dec. 22; 319(25): 1676-80. (Rosenberg S A, Packard B S, Aebersold P M, et al. Use of tumor-infiltrating lymphocytes and interleukin-2 in the immunotherapy of patients with metastatic melanoma. A preliminary report. N Engl J Med 1988; 319:1676. (Robert Dillman et al., Tumor-Infiltrating Lymphocytes and Interleukin-2: Dose and Schedules of Administration in the Treatment of Metastatic Cancer; Cancer Biotherapy & Radiopharmaceuticals. December 2004, Vol. 19, No. 6: 730-737. (Rosenberg S A, Speiss P, Lafreniere R. A new approach to the adoptive immuno-therapy of cancer with tumor-infiltrating lymphocytes. Science. 1986; 233:1318-1321.) The majority of the clinical data regarding TIL therapy comes from melanoma studies (Rosenberg S A, Packard B S, Arebersold P M, et al. Use of tumor infiltrating lymphocytes and interleukin-2 in the immunotherapy of patients with metastatic melanoma: a preliminary report. N Engl J. Med. 1988; 319:1676-1680.) These studies show that TILs can circulate in patients for extended periods of time and that they selectively migrate to the tumor and sites of metastases.

Natural killer (NK) cells belong to the innate immune system and efficiently kill virus-infected and tumor cells. NK killing is restricted mainly to cells that have lost class I MHC expression, a phenomenon known as the missing self. NK cell cytotoxicity is tightly regulated by various inhibitory, class I MHC-recognizing receptors. The inhibitory signal is delivered via the immuno-receptor tyrosine-based inhibitory motif (ITIM) sequences found within the cytosolic tail of these receptors. Families of class I MHC binding inhibitory receptors include members of the Ig superfamily, namely killer Ig-related two-domain long-tail (p58) and three-domain long-tail (p70) receptors, the C-type lectin complex CD94/NKG2A, and the leukocyte Ig-like receptor (Ig-like transcript) family.

There are also other NK-specific receptors, termed natural cytotoxicity receptors (NCRs), which are directly involved in triggering NK cell cytotoxicity. The NCR group consists of several proteins, including NKp30, NKp44, NKp46, NKp80, and CD16. The cellular lysis ligands for all the NCRs have yet to be identified. A viral ligand (hemagglutinin) was shown to interact with the NKp46 receptor, and this interaction resulted in the enhancement of lysis of certain virus-infected cells. Indeed, the killing activity of target cells by human natural killer (NK) cells is mediated via a panel of lysis receptors of which is included CD16, NKp30, NKp44, NKp46, and NKG2D. These receptors recognize viral ligands such as hemagglutinin, stress-induced ligands such as MHC class I chain-related antigen A (MICA) and MICB, or other as-yet-undefined, cellular ligands. As mentioned, cells are protected from lysis by NK cells mainly owing to the interactions between class I MHC proteins and the appropriate inhibitory NK receptors.

A novel class I MHC-independent inhibitory mechanism of human NK cytotoxicity, mediated via the carcinoembryonic antigen-related cell adhesion molecule 1 (CEACAM1) homotypic interactions has been identified. Furthermore, it has been demonstrated that the CEACAM1 protein plays a pivotal role in the inhibition of killing, proliferation, and cytokine secretion of interleukin 2 (IL-2)-activated decidual NK, T, and NKT cells, respectively.

Once class I MHC proteins are removed from the cell surface, these cells become susceptible to NK cell attack. It was surprising to learn that patients with transporter associated with antigen processing (TAP2) deficiency do not frequently suffer from autoimmune manifestations at early stages of their life. Activated NK cells derived from such patients may either be expressing an unknown inhibitory mechanism or are missing an unidentified lysis receptor. NK tolerance toward self-cells might be controlled by similar mechanisms.

The present inventors have demonstrated that the expression of the NKp46 receptor is severely impaired in a newly identified TAP2-deficient family and that the vast majority of activated NK cells derived from these patients use the CEACAM1 protein interactions to avoid tumor and autologous cell killing.

The present inventors have also shown that many of the CD16-negative NK clones inefficiently kill 1106mel cells because of the CD66a homotypic interactions The inhibition of NK cell cytotoxicity by CD66a was dependent on the level of CD66a expression on both effector and target cells. 721.221 cells expressing CD66a protein were protected from lysis by CD66a-expressing NK and YTS cells. Redirected lysis experiments performed by the present inventors showed that the strength of the inhibition is dependent on the level of CD66a expression on NK cells. A dramatic increase in CD66a expression was observed among NK cells isolated from melanoma patients. As stated above, a novel class I MHC-independent inhibitory mechanism of human NK cell cytotoxicity has been demonstrated by the present inventors. Some melanoma tumors may use this mechanism to avoid attack by NK cells.

Human natural killer (NK) cells are able to eliminate a broad spectrum of tumors and virus-infected cells by using several receptors, such as CD16, NKp30, NKp44, NKp46 and NKG2D. These receptors recognize either viral ligands, such as hemagglutinin, stress induced ligands, such as MICA and MICB, or other yet-undefined cellular ligands. Other NK receptors mediate inhibition of the killing activity following interaction with MHC class I proteins present on normal cells. Removal of MHC class I proteins from the cell surface renders it susceptible to NK cell attack through the phenomenon known as the "missing self".

Additional receptors are also able to manipulate NK cell cytotoxicity and the present inventors have shown a novel MHC class I independent inhibitory mechanism of human NK cytotoxicity that is mediated by the CEACAM1 homophilic interactions. This CEACAM1-mediated inhibition might play an important role in the in vivo development of melanoma in human patients. A 10-year follow-up study correlated the presence of CEACAM1 on primary melanoma lesions with poor survival. In addition, the present inventors have demonstrated the pivotal role of the CEACAM1 in the inhibition of killing, cytokine secretion and proliferation of activated decidual NK, NKT and T cells, respectively. The present inventors have also provided substantial evidence for a major role of the inhibitory CEACAM1 interactions in controlling NK cell autoreactivity in TAP2-deficient patients.

The presence of human soluble CEACAM1 protein can be observed in the serum of healthy donors. Furthermore, variations in serum levels of the soluble CEACAM1 protein are observed in various pathologies. For example, increased CEACAM1 levels were observed in the sera of patients with various hepatic diseases such as obstructive jaundice, primary billiary cirrhosis, autoimmune hepatitis and cholangiocarcinoma. A decrease in the soluble CEACAM1 level has not been reported.

It has also been demonstrated that the soluble CEACAM1 protein blocks the CEACAM1-mediated inhibition of NK cell killing activity in a dose-dependent manner. Moreover, the present inventors have demonstrated that serum CEACAM1 levels among the TAP2-deficient patients are decreased when compared to normal individuals. These findings concur with the dominant role of the CEACAM1-mediated inhibition in controlling NK autoreactivity in TAP2-deficient patients. Thus, the maximal compensatory effect of CEACAM1-mediated inhibition is attained.

The human carcinoembryonic Ag (CEA)3 protein family encompasses several forms of proteins with different biochemical features. These proteins are encoded by 29 genes tandemly arranged on chromosome 19q13.2. CEA family genes have been classified into two major subfamilies, the CEA cell adhesion molecule (CEACAM) and the pregnancy-specific glycoprotein subgroups. The CEACAM proteins, which are part of the larger Ig superfamily, include CEACAM1, -3, -4, -5, -6, -7, and -8. They share a common basic structure of sequentially ordered different Ig-like domain(s) and are able to interact with each other. For example, it was reported that various CEACAM proteins, such as CEACAM1 or CEACAM5, exhibit both homophilic and heterophilic interactions.

CEACAM1 (CD66a), a transmembrane protein and member of the carcinoembryonic Ags family, contains two ITIM sequences located within its cytosolic tail, and interacts in a homotypic/heterotypic manner with other known CD66 proteins, including CD66a, CD66c, and CD66e proteins. It is expressed on a wide spectrum of cells, ranging from epithelial to hemopoietic origin. Among CD66 proteins tested, the CD66a protein only is expressed on the surface of activated, CD16-negative NK cells.

The various CEACAM proteins have different biochemical features, such as anchorage to cell surface (GPI-linked, transmembrane or secreted forms), length of cytoplasmic tail (long or short), and the presence or absence of various signal transduction motifs. These proteins are actively involved in numerous physiological and pathological processes.

CEACAM1 is a transmembrane protein that can be detected on some immune cells as well as on epithelial cells. Many different functions have been attributed to the CEACAM1 protein. It was shown that the CEACAM1 protein exhibits antiproliferative properties in carcinomas of colon, prostate, as well as other types of cancer. Additional data support the central involvement of CEACAM1 in angiogenesis and metastasis. CEACAM1 also has a role in the modulation of innate and adaptive immune responses. The present inventors have shown that CEACAM1 homophilic interactions inhibit NK-mediated killing activity independently of MHC class I recognition. This novel mechanism plays a pivotal role in the inhibition of activated decidual lymphocytes in vitro and most likely also in vivo after infection, including for example CMV infections. The CEACAM1 homophilic interactions are probably important in some cases of metastatic melanoma, as increased CEACAM1 expression was observed on NK cells derived from some patients compared with healthy donors. There is a clear association of CEACAM1 expression on primary cutaneous melanoma lesions with the development of metastatic disease and poor survival. The present inventors have demonstrated the role of CEACAM1-mediated inhibition in maintaining NK self-tolerance in TAP2-deficient patients. Additional reports have indicated that CEACAM1 engagement either by TCR cross-linking with mAb or by *Neisseria gonorrhoeae* Opa proteins inhibits T cell activation and proliferation.

As stated above, the CEACAM1 protein interacts with other CEACAM protein family members, such as CEACAM1 itself and CEACAM5. At least part or the entire binding site of human CEACAM1 is located at the N-terminal Ig-V-type domain of the CEACAM1 protein. In particular, amino acids 39V and 40D and the salt bridge between 64R and 82D may play an important role in this binding. Most amino acid sequences of the N-terminal domain of CEACAM1, -3, -5, and -6 are identical, and predicted binding residues are conserved among the four proteins. These proteins might interact with each other. This is of particular importance, because in certain tumors the CEACAM1 protein is down-regulated, followed by upregulation of CEACAM6 protein expression.

The present inventors have demonstrated the inability of CEACAM1 to bind CEACAM6. The present inventors have also directly shown that the presence of both residues 43R and 44Q in the CEACAM1 is crucial for the homophilic CEACAM1 interaction and that substitution of these residues with the 43S and 44L residues that are present in CEACAM6 abolishes the inhibitory effect. The reciprocal substitution of 43S and 44L of CEACAM6 to the 43R and 44Q residues, respectively, results in the gain of inhibitory heterophilic interactions with the CEACAM1 protein. Thus, the dichotomy of CEACAM family members by recognition of CEACAM1 is determined by the presence of R and Q at positions 43 and 44.

BRIEF SUMMARY OF THE INVENTION

One object of the present invention is to provide methods and compositions for the regulation of the immune system and specific immune responses. Another object of the present invention is to provide methods and compositions for the regulation of lymphocyte activity. A still further object of the present invention is to provide methods and compositions for enhancing the efficacy of tumor-infiltrating lymphocyte (TIL) therapy in the treatment of cancer.

One or more of the preceding objects, or one or more other objects which will become plain upon consideration of the present specification, are satisfied by the invention described herein.

One aspect of the invention, which satisfies one or more of the above objects, is the functional modulation of at least one protein from the CEACAM protein family. Another aspect of the invention, which satisfies one or more of the above objects, is the negative functional modulation of the CEACAM1 (cd66a) protein.

Another aspect of the present invention provides methods for enhancing the efficacy of Tumor Infiltrating Lymphocyte cancer therapy that comprise the modulation of CEACAM1 protein function.

Another aspect of the present invention provides methods for enhancing the efficacy of Tumor Infiltrating Lymphocyte cancer therapy that comprises decreasing the effective concentration of CEACAM1 functional protein.

A still further aspect of the present invention provides methods for enhancing the efficacy of Tumor Infiltrating Lymphocyte cancer therapy comprising the enrichment of a Tumor Infiltrating Lymphocyte cell population for cells lacking CEACAM1.

Another aspect of the present invention provides methods for treating cancer in a human patient comprising the step of administering to the patient a therapeutically effective amount of a composition comprising a CEACAM1 binding agent conjugated to a chemotherapeutic.

A still further aspect of the present invention provides methods for diagnosing a cancer in a human patient, wherein the method comprises the step of contacting a biological sample, derived from a patient suspected of having cancer, with a CEACAM1 binding agent conjugated to a detectable moiety and/or an affinity moiety.

A still further aspect of the present invention provides methods for diagnosing a cancer in a human patient, wherein the method comprises the step of injecting into the patient a CEACAM1 binding agent conjugated to a detectable moiety.

DETAILED DESCRIPTION OF THE INVENTION

While the invention will be described in connection with one or more embodiments, it will be understood that the invention is not limited to those embodiments. On the contrary, the invention includes all alternatives, modifications, and equivalents as may be included within the spirit and scope of the appended claims.

The presently described technology relates to methods and compositions for the regulation of the immune system and specific immune responses, and in particular to methods and compositions for the regulation of lymphocyte activity. One object of the presently described technology provides methods and compositions for enhancing the efficacy of tumor-infiltrating lymphocyte (TIL) therapy in the treatment of cancer.

One aspect of the present invention is the functional modulation of at least one member of the CEACAM protein family. The CEACAM protein family, which are part of the larger Ig superfamily, include without limitation CEACAM1, -3, -4, -5, -6, -7, and -8. The CEACAM protein family share a common basic structure of sequentially ordered different Ig-like domain(s) and are able to interact with each other.

In one embodiment of the presently described invention, regulation of the immune system and/or one or more specific immune responses is achieved by the negative modulation of CEACAM1 (cd66a) function. The negative modulation of CEACAM1 function can include the disruption of a CEACAM1 homotypic or heterotypic protein-protein interaction. The negative modulation of CEACAM1 function can include for example contacting CEACAM1 with a CEACAM1 specific binding element. The modulation of CEACAM1 function can also include for example contacting a protein interacting with the CEACAM1 protein with specific binding element or agent to inhibit or disrupt formation of a target CEACAM1 protein-protein interaction.

These elements or agents include but are not limited to linear or cyclic nucleic acids, full-length proteins, protein structural or functional domains, smaller peptides, and peptidomimetic derivatives. The terms "amino acid sequence," "nucleic acid sequence," "protein," "polypeptide," "peptide" and "nucleic acid" include compositions of the invention that also include "analogs," or "conservative variants" and "mimetics" such as "peptidomimetics" with structures and activity that substantially correspond to the compound from which the variant was derived. These agents can be derived from any protein that participates in any CEACAM family homotypic and/or heterotypic protein-protein interaction, or any other protein including but not limited to immunoglobins having binding specificity to a CEACAM family protein.

In certain embodiments of the present invention, the elements or agents employed to disrupt a CEACAM family protein-protein interaction to effect control over a particular immune response can include but are not limited to a full length CEACAM family protein, or a fragment derived therefrom. CEACAM family proteins that can be used as include but are not limited to the CEACAM1 protein represented by SEQ ID No. 1; the CEACAM3 protein represented by SEQ ID No. 2; the CEACAM5 protein represented by SEQ ID No. 3; the CEACAM6 protein represented by SEQ ID No. 4; and the CEACAM8 protein represented by SEQ ID No. 5. In another embodiment of the present invention, the agent employed to disrupt a CEACAM family protein-protein interaction to effect control over a particular immune response can comprise any immunoglobulin, or fragment thereof, specific for the CEACAM family protein or protein interacting with the CEACAM family protein.

In still other embodiments of the present invention, the elements or agents employed to disrupt a CEACAM family protein-protein interaction to effect control over a particular immune response comprises a small molecule compound. The term "small molecule" means any synthetic small molecule, such as an organic molecule, inorganic molecule, or synthetic molecule, such as those generated by combinatorial chemistry methodologies. These small molecules can be synthesized using a variety of procedures and methodologies, which are well described in the scientific and patent literature, e.g., Organic Syntheses Collective Volumes, Gilman et al. (Eds) John Wiley & Sons, Inc., NY; Venuti (1989) *Pharm Res.* 6:867-873. Synthesis of small molecules, as with all other procedures associated with this invention, can be practiced in conjunction with any method or protocol known in the art. For example, preparation and screening of combinatorial chemical libraries are well known, see, e.g., U.S. Pat. Nos. 6,096,496; 6,075,166; 6,054,047; 6,004,617; 5,985,356; 5,980,839; 5,917,185; 5,767,238.

In still other embodiments of the present invention, the elements or agents employed to disrupt a CEACAM family protein-protein interaction to effect control over a particular immune response comprises a multimer agent comprising at least two or more agents according to the present invention, linked together. The agents, linked together to form the multimer agent, can be identical or different, and can include but are not limited to any combination protein, nucleic acid, small molecules, or derivatives thereof.

In another embodiment of the presently described invention, regulation of the immune system and/or one or more specific immune responses includes the negative or positive modulation of CEACAM1 gene expression or translation of CEACAM1 mRNA. The modulation of CEACAM1 gene expression or CEACAM1 mRNA translation can involve contacting a population of cells with a protein, nucleic acid, small molecule, or any combination thereof. In another embodiment of the presently described invention, regulation of the immune system and/or one or more specific immune responses comprises the negative or positive modulation of CEACAM1 gene expression or translation of CEACAM1 mRNA. The modulation of CEACAM1 gene expression or CEACAM1 mRNA translation can comprise any number of techniques know to those skilled in the art for the modulation of gene expression, and can involve contacting any environment with a protein, peptide, peptidomimetic, nucleic acid, nucleic acid analog, small molecule, or some combination thereof.

In a further aspect of the presently described invention, there are provided methods and/or compositions for modulating the immune system and/or one or more specific immune responses in the course of treating a disease. Exemplar diseases include cancers, autoimmune conditions, and those diseases requiring tissue transplantation.

One aspect of the present invention provides methods and/or compositions for enhancing the efficacy of tumor-infiltrating lymphocyte (TIL) therapy in the treatment of cancer. In one embodiment of this aspect of the present invention, the efficacy of TIL therapy for the treatment of cancer is enhanced by the negative modulation of the functional activity of at least one member of the CEACAM protein family. In one preferred embodiment of this aspect of the present invention, the efficacy of TIL, therapy for the treatment of cancer is enhanced by the negative modulation of CEACAM1 protein functional activity. The negative modulation of the at least one member from the CEACAM protein family, including but not limited to the CEACAM1 protein, can be accomplished by any number of techniques know to those skilled in the art for the negative modulation of protein function, including but not limited to the allosteric or non allosteric disruption of a homotypic or heterotypic protein-protein interaction.

Certain aspects of the present invention can be performed in situ, in vivo, or in vitro. For example, the methods and/or compositions of the present invention can be employed in a cell culture, including for example a population of Tumor Infiltrating Lymphocytes. The methods and/or compositions of the present invention may also be employed in the living body of an animal, such as a human.

In one preferred aspect of the present invention, the efficacy of TIL therapy for the treatment of cancer is enhanced by the negative modulation of CEACAM1 (cd66a) protein function in a population of tumor-infiltrating lymphocytes. In one embodiment of this aspect of the present invention, the efficacy of TIL therapy for the treatment of cancer is enhanced by the disruption of a homotypic and/or heterotypic CEACAM1 protein-protein interaction by contacting a population of tumor-infiltrating lymphocytes with CEACAM1 selective binding elements.

One object of the present invention includes methods and/or materials for controlling immunity and/or an immune response that involves the modulation of CEACAM1 function. The CEACAM1 protein may or may not be membrane bound. The modulation of CEACAM1 function can include, for example, the addition of a protein, peptide, peptidomimetic, nucleic acid, nucleic acid analog, small molecule, or any combination thereof. The CEACAM1 protein itself, in addition to any peptide or peptidomimetic derived from the CEACAM1 protein, or any immunoglobulin specific for CEACAM1, or any combination thereof, can be used to modulate CEACAM1 function. Also, a CEACAM1 binding partner can itself, in addition to any peptide or peptidomimetic derived from a CEACAM1 binding partner, or any immunoglobulin specific for a CEACAM1 binding partner, or any combination thereof, can be used to modulate CEACAM1 function.

Another aspect of the present invention provides methods for enhancing the efficacy of Tumor Infiltrating Lymphocyte cancer therapy that comprise the modulation of CEACAM1 protein function. The method of this aspect of the present invention can be performed in situ, in vivo, or in vitro. For example the method of this aspect of the present invention can be performed in a cell culture comprising a population of Tumor Infiltrating Lymphocytes. One embodiment of this aspect of the present invention comprises the disruption of a target CEACAM1 homotypic or heterotypic protein-protein interaction. The disruption of the target CEACAM1 homotypic or heterotypic protein-protein interaction comprises contacting at least one protein involved in the protein-protein interaction with an inhibitory agent that partially or completely inhibits or disrupts the protein-protein interaction. The inhibitory agent can comprise any an amino acid sequence, nucleic acid sequence, small molecule compound, or combinations thereof. The inhibitory agent can include but is not limited to any amino acid sequence derived from a CEACAM family protein sequence, including but not limited to sequences derived from the CEACAM1 protein. The inhibitory agent can also comprise an immunoglobulin or fragment thereof having specificity to at least one of the proteins involved in the CEACAM1 homotypic or heterotypic protein-protein interaction. The inhibitory agent that partially or completely inhibits or disrupts said protein-protein interaction can also be conjugated with a protein-crosslinking moiety.

Another aspect of the present invention provides methods for enhancing the efficacy of Tumor Infiltrating Lymphocyte cancer therapy that comprises decreasing the effective concentration of CEACAM1 functional protein. One embodiment of this aspect of the present invention comprises the inhibition of CEACAM1 gene expression, protein synthesis, protein stability, or combinations thereof. The method of this aspect of the present invention can be performed in situ, in vivo, or in vitro. For example the method of this aspect of the present invention can be performed in a cell culture comprising a population of Tumor Infiltrating Lymphocytes.

A still further aspect of the present invention provides methods for enhancing the efficacy of Tumor Infiltrating Lymphocyte cancer therapy comprising the enrichment of a Tumor Infiltrating Lymphocyte cell population for cells lacking CEACAM1. One embodiment of this aspect of the present invention comprises contacting the Tumor Infiltrating Lymphocyte cell population with a CEACAM1 binding element. The CEACAM1 binding element can include but is not limited to an anti-CEACAM1 immunoglobulin or fragment thereof. The CEACAM1 binding element can also include but is not limited to any amino acid sequence derived from a CEACAM family protein sequence, including but not limited to sequences derived from the CEACAM1 protein. The CEACAM1 binding element of this aspect of the present invention can be labeled with a detectable moiety, an affinity-tag moiety, or both. In certain embodiments of this aspect of the present invention the Tumor Infiltrating Lymphocyte cell population is subjected to affinity purification, cell sorting, or both. In still other embodiments of this aspect of the present invention the Tumor Infiltrating Lymphocyte cell population is contacted with an anti-CEACAM1 immunoglobulin and complement. In a still further embodiment of this aspect of the present invention the Tumor Infiltrating Lymphocyte cell population is contacted with a CEACAM1 binding element conjugated to a cell toxin.

Another aspect of the present invention provides methods for treating cancer in a human patient comprising the step of administering to the patient a therapeutically effective amount of a composition comprising a CEACAM1 binding agent conjugated to a chemotherapeutic. The CEACAM1 binding agent includes but is not limited to any amino acid sequence derived from a member of the CEACAM protein family, including but not limited to the CEACAM1 protein. The CEACAM1 binding agent can also comprise an anti-CEACAM1 immunoglobulin or fragment thereof. The CEACAM1 binding agent can also comprise a peptidomimetic or small molecule compound. The chemotherapeutic can include but is not limited to a cytotoxin, a chemokine, a pro-apoptotic, interferon, a radioactive moiety, or combinations thereof. In preferred embodiments of this aspect of the present invention, the chemotherapeutic moderates cellular metabolism. For example, the chemotherapeutic can moderate or alter nucleic acid metabolism, protein metabolism, cell division, DNA replication, purine biosynthesis, pyrimidine biosynthesis, amino acid biosynthesis, gene expression, mRNA processing, protein synthesis, apoptosis, or combinations thereof.

A still further aspect of the present invention provides methods for diagnosing a cancer in a human patient, wherein the method comprises the step of contacting a biological sample, derived from a patient suspected of having cancer, with a CEACAM1 binding agent conjugated to a detectable moiety and/or an affinity moiety. The CEACAM1 binding agent can comprise any amino acid sequence derived from a member of the CEACAM protein family, including but not limited to amino acid sequences derived from CEACAM1. The CEACAM1 binding agent can also comprise an anti-CEACAM1 immunoglobulin or fragment thereof. The CEACAM1 binding agent can also comprise a peptidomimetic or small molecule compound. The detectable moiety of this aspect of the present invention can comprise a fluorescent molecule, a radioactive molecule, or some combination thereof. The affinity moiety of this aspect of the present invention includes but is not limited to a magnetic particle.

A still further aspect of the present invention provides methods for diagnosing a cancer in a human patient, wherein the method comprises the step of injecting into the patient a CEACAM1 binding agent conjugated to a detectable moiety. The CEACAM1 binding agent can comprise any amino acid sequence derived from a member of the CEACAM protein family, including but not limited to amino acid sequences derived from CEACAM1. The CEACAM1 binding agent can also comprise an anti-CEACAM1 immunoglobulin or fragment thereof. The CEACAM1 binding agent can also comprise a peptidomimetic or small molecule compound. The detectable moiety of this aspect of the present invention can comprise a fluorescent molecule, a radioactive molecule, or some combination thereof. In certain other embodiments of this aspect of the present invention, the CEACAM1 binding agent conjugated to a detectable moiety is ingested by the human patient.

What is claimed is:

1. A method for detecting CEACAM1 expression in a cancer patient, said method comprising the step of contacting a biological sample having Tumor Infiltrating Lymphocytes expressing CEACAM1 with both CEACAM1 labeled with a detectable moiety and an anti-CEACAM1 antibody labeled with a detectable moiety.

2. The method of claim 1, wherein said detectable moiety comprises a fluorescent molecule, or a radioactive molecule, or a magnetic particle, or some combination thereof.

* * * * *